US00PP09479P

United States Patent [19]

Challet

[11] Patent Number: Plant 9,479

[45] Date of Patent: Mar. 19, 1996

[54] CHRYSANTHEMUM PLANT NAMED 'CHAKUSE'

[75] Inventor: Jean-Pierre Challet, Lafayette, Calif.

[73] Assignee: Selection New Plant Sarl, Le Cannet des Maures, France

[21] Appl. No.: 273,993

[22] Filed: Jul. 12, 1994

[51] Int. Cl.[6] ..... A01H 5/00

[52] U.S. Cl. ..... Plt./78

[58] Field of Search ..... Plt./78, 82.2

[56] References Cited

U.S. PATENT DOCUMENTS

| | | | |
|---|---|---|---|
| P.P. 6,948 | 7/1988 | VandenBerg | Plt./78 |
| P.P. 7,586 | 7/1991 | VandenBerg | Plt./78 |
| P.P. 8,704 | 4/1994 | Machin | Plt./78 |
| P.P. 8,804 | 6/1994 | VandenBerg | Plt./78 |
| P.P. 8,843 | 7/1994 | VandeBerg | Plt./78 |

*Primary Examiner*—Howard J. Locker
*Attorney, Agent, or Firm*—Burns, Doane, Swecker & Mathis

[57] ABSTRACT

A new and distinct Chrysanthemum cultivar named 'Chakuse' is provided. The new cultivar was the result of a controlled breeding program. Attractive double bright yellow blossoms of the spider type are formed in profusion (as illustrated). The response period of the flowers is approximately eight and one-half weeks. Recurrent flower production throughout the year is possible. The plant possesses strong stems, forms attractive leaves, and commonly assumes a height of only approximately 25 to 30 cm. The new cultivar is particularly suited for use in the production of a decorative pot Chrysanthemum. No growth regulator is required to achieve the short plant height.

3 Drawing Sheets

SUMMARY OF THE INVENTION

The present invention comprises a new and distinct cultivar of Chrysanthemum, botanically known as *Dendranthema grandiflora,* and hereinafter is referred to by the cultivar name 'Chakuse'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during October 1984 at Nuaille, Trementines, France. The female parent (i.e., the seed parent) was the 'Fada' cultivar (non-patented in the United States) having double flat purple blossoms that was created in France by a breeder named Bernard, and the male parent (i.e., the pollen parent) was the 'Domi' cultivar (non-patented in the United States) that is an old French cultivar having honey-colored blossoms in an anemone spray configuration. The parentage of the new cultivar can be summarized as follows:

'Fada'×'Domi'.

The seeds resulting from the above pollination were sown and many small plantlets were obtained which were physically and biologically different from each other. Selective study resulted in the identification of a single plant of the new variety.

It was found that the new cultivar of the present invention:

(a) exhibits in profusion attractive double bright yellow spider blossoms with upright petals,
(b) exhibits a flower response period of approximately eight and one-half weeks,
(c) is highly amenable to branching by pinching,
(d) achieves a short plant height, and
(e) is particularly suited for pot mum production on a recurrent basis throughout the year.

The new cultivar is intended primarily as a decorative pot spider Chrysanthemum for growing indoors. However, the new cultivar can be grown outdoors at temperatures above freezing.

In the absence of debudding a profusion of blossoms form per stem (as illustrated). A greatly increased number of branches readily can be induced by pinching. The pinching of a cutting commonly produces 5 or more stems. No growth regulator is required to produce the short plant height.

The new cultivar can be considered to be an October-flowering greenhouse variety with the natural flowering season commonly occurring in weeks 41 and 42 of the year. Attractive blossoms can be produced on a recurrent basis throughout the year with the indicated eight and one-half week response period. The blossoms commonly last at least one and one-half weeks on the plant, and commonly less than one week when placed in a vase. Sometimes the blossoms become daisy-eyed with age.

Asexual reproduction of the new cultivar by cuttings initially taken during 1985, as performed in Nuaille, Trementines, France, in a controlled environment has demonstrated that the characteristics of the new cultivar as herein described are firmly fixed and are retained through successive generations of asexual propagation.

'Chakuse' has not been observed under all possible environmental conditions to date. Accordingly, it is possible that the phenotype may vary somewhat with variations in the environment, such as temperature, light, day length, contact with pesticides and/or subjection to growth retardant treatments.

The 'Chakuse' cultivar can be readily distinguished from the 'Chakara' cultivar (copending U.S. Plant patent application Ser. No. 08/273,994, filed Jul. 12, 1994) that was produced by the cross of the same parent cultivars. More specifically, the new 'Chakuse' cultivar exhibits a yellow spider capitulum and the 'Chakara' cultivar exhibits a bright bronze anemone capitulum, the 'Chakuse' cultivar exhibits a bushy growth habit unlike the 'Chakara' cultivar, the 'Chakuse' cultivar exhibits ray florets having rounded tips while those of 'Chakara' are dentated, the 'Chakuse' cultivar exhibits tubular disc florets while those of the 'Chakara' cultivar are petaloid, and the 'Chakuse' cultivar exhibits a response period of approximately eight and one-half weeks and the 'Chakara' cultivar exhibits a lesser response period of approximately eight weeks.

Mutations of the sister 'Chakara' cultivar are the 'Chaplou' cultivar (copending U.S. Plant patent application Ser. No. 08/273,992, filed Jul. 12, 1994) and the 'Chaprila' cultivar (copending U.S. Plant patent application Ser. No. 08/274,001, filed Jul. 12, 1994). Each of these additional cultivars exhibits an anemone capitulum unlike the spider capitulum of the 'Chakuse' cultivar of the present invention.

The new 'Chakuse' cultivar of the present invention is being marketed under the SUN trademark.

BRIEF DESCRIPTION OF THE PHOTOGRAPHS

The accompanying photographs were prepared during June, 1994, and show as nearly true as it is reasonably possible to make the same in color illustrations of this character, typical plants and plant parts of the new cultivar of the present invention. The plants were 13 weeks of age and were grown at Nuaille, Trementines, France, under standard greenhouse conditions which approximate those commonly utilized for the production of decorative pot mums. The plants had been pinched once and had not been disbudded. No growth regulant was utilized. Any labels shown in the photographs are 2.5 cm. in width and can be used for size comparisons.

DETAILED DESCRIPTION

Figure 1:
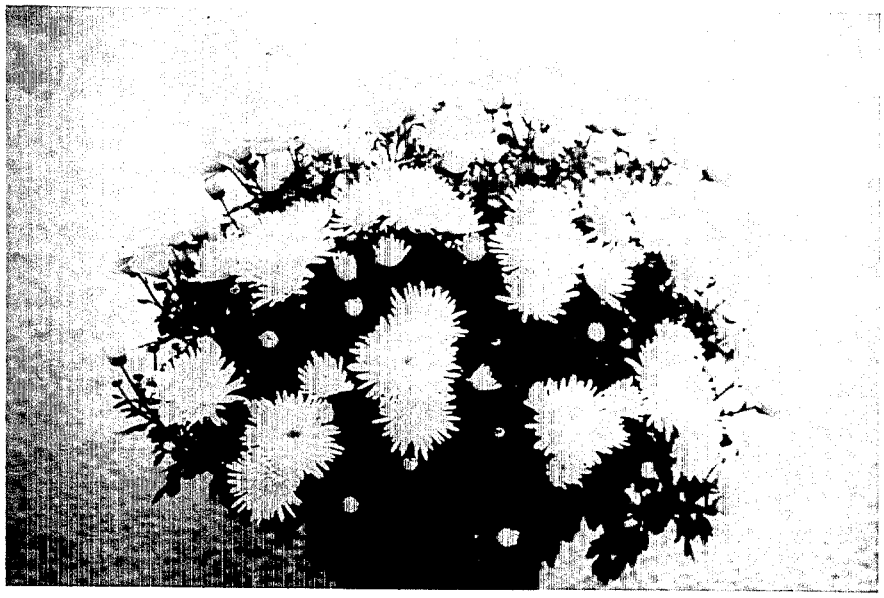
FIG. 1 illustrates typical specimens of the overall plant wherein three cuttings were placed in a 20 cm. pot. The bright yellow spider flowers, as well as the foliage, are apparent.
Figure 2:
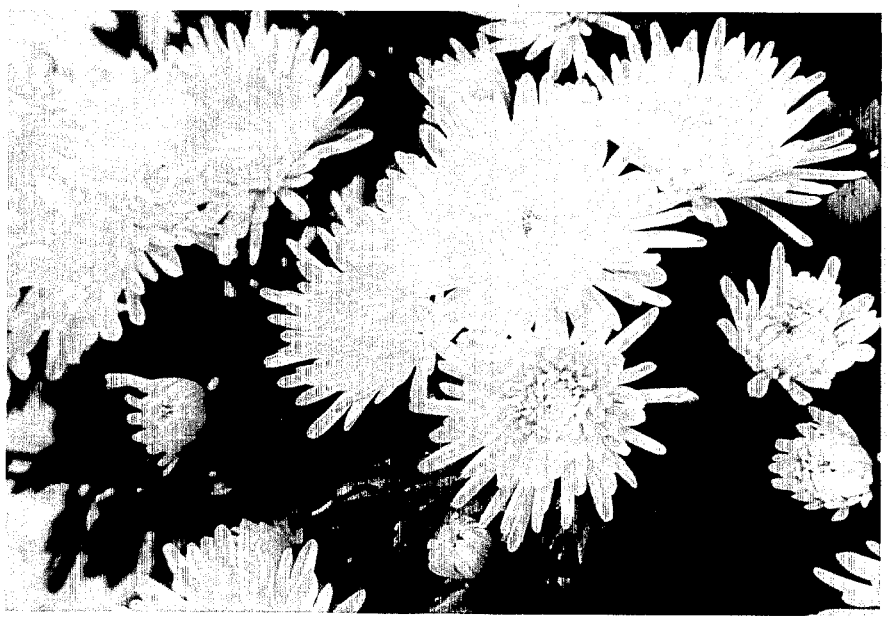
FIG. 2 illustrates a closer view of typical flowers in various stages of opening.
Figure 3:
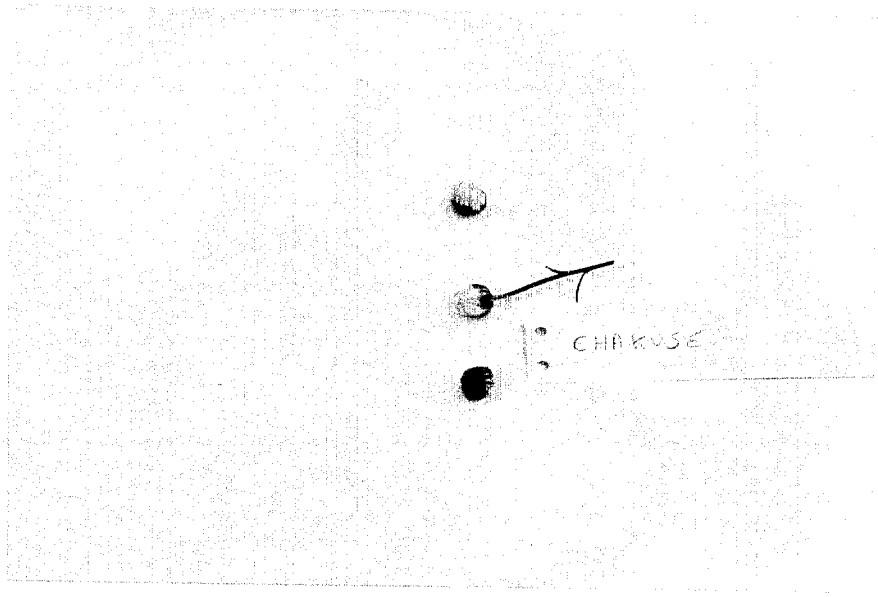
FIG. 3 illustrates from top to bottom, upper, side, and under views of largely unopened buds.
Figure 4:
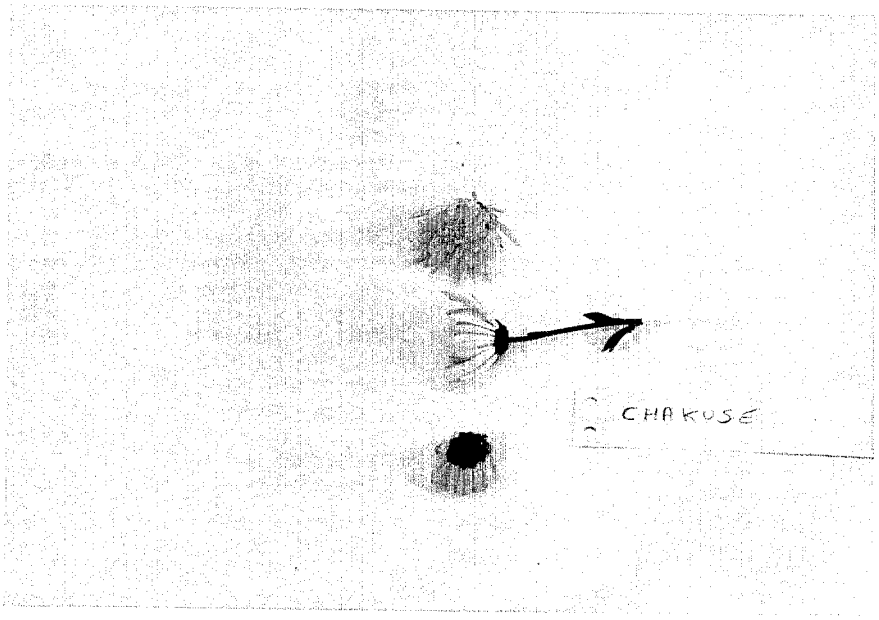
FIG. 4 illustrates from top to bottom, upper, side, and under views of the flowers in the course of opening.
Figure 5:
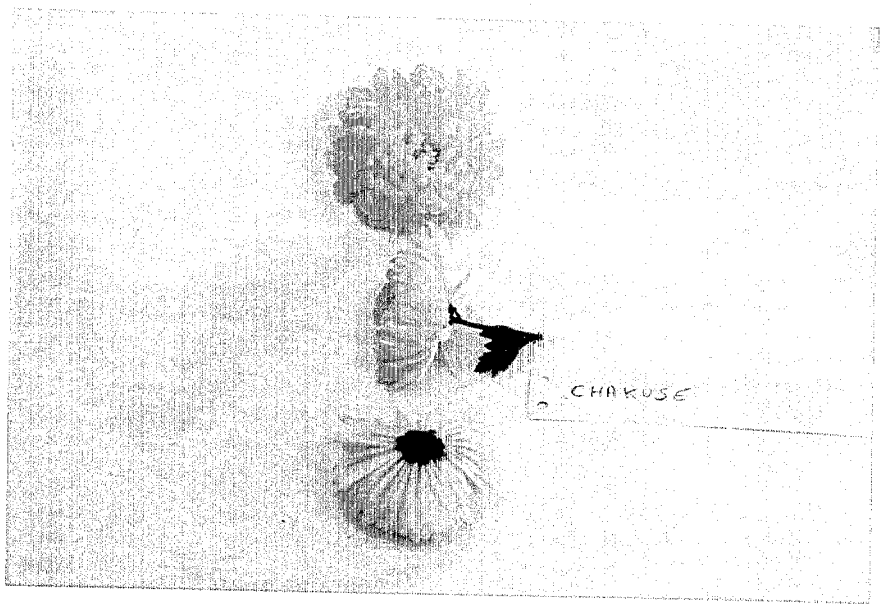
FIG. 5 illustrates from top to bottom, upper, side, and under views of fully open flowers.
Figure 6:
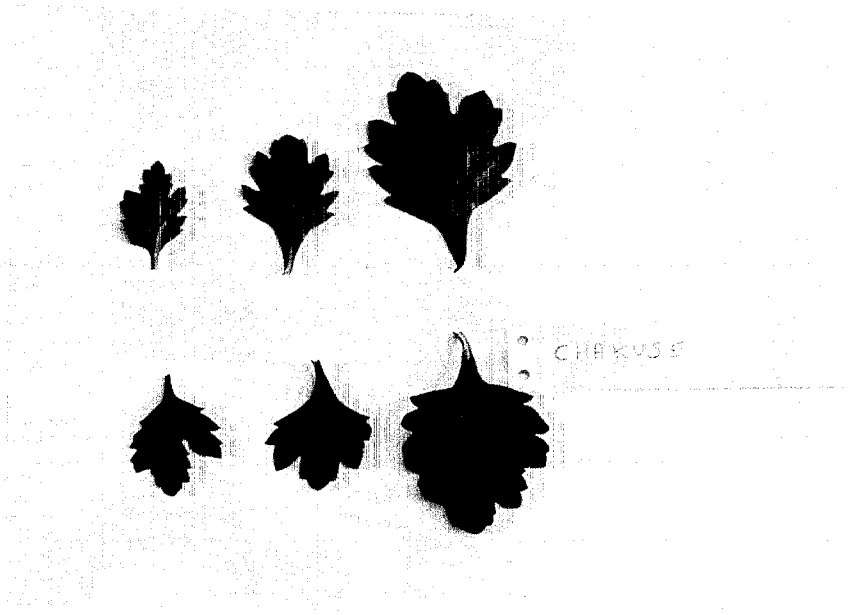
FIG. 6 illustrates at the top row the under surface of typical leaves of various sizes and at the bottom row the upper surfaces of typical leaves of various sizes.

The chart used in the identification of colors described hereafter is the R.H.S. Colour Chart of The Royal Horticultural Society, London, England. In some instances more common color terms are provided and are to be accorded their usual dictionary significance. The plants described were 13 weeks of age and were grown at Nuaille, Trementines, France, under standard greenhouse conditions which approximate those commonly utilized for the production of decorative pot mums.

Classification:

*Botanical.*—*Dendranthema grandiflora,* cv. 'Chakuse'.

*Commercial.*—Decorative pot mum.

Inflorescence

A. Capitulum:

*Type.*—Spider.

*Diameter across face.*—Medium, approximately 9 to 10 cm. on average when fully expanded.

*Frequency.*—Corymbiform, and blossoms form in profusion (as illustrated). Night temperatures above 23° C. will delay flowering. Night temperatures as low as 14° C. generally can be tolerated, and even night temperatures as low as 5° to 10° C. can be tolerated during the bud opening stage.

B. Corolla of ray and disc florets:

*Disc florets.*—Tubular, yellow in coloration, short to medium in length, numerous, a few tend to be scattered among the ray florets, but most form a cluster at the apex of the receptacle that is visible when the flower head fully matures.

*General tonality.*—Bright yellow capitulum that tends to lose some brightness as the blossoms fully mature.

*Color ray florets.*—Before anther dehiscence, Yellow Group 7B, and at anther dehiscence, Yellow Group 9A but more intense on the inside and Yellow Group 7B on the outside.

*Configuration ray florets.*—Concave and sometimes rolled in cross section, rough in texture, generally short and straight petals, high to very high length to width ratio in the outer row of ray florets, and possess rounded tips.

C. Reproductive organs:

*Androecium.*—Generally present with disc florets and absent in ray florets.

*Gynoecium.*—Generally present with most disc florets and with most ray florets.

*Pollen.*—Present, and golden-yellow in coloration.

*Fragrance.*—Typical of Chrysanthemum.

Plant

A. General appearance:

*Height.*—Short, and approximately 25 to 30 cm. in height on average at 10 weeks of age.

*Growth habit.*—Bushy.

B. Foliage:

*Color (upper surface).*—Green Group 137C to 143C, with the older inside leaves that do not receive as much light tending to be more yellowish.

*Color (under surface).*—Generally lighter green, approaches Green Group 138A.

*Long day leaf count.*—Approximately 17 to 22 leaves per typical stem in a long day crop before the bud occurs.

*Configuration.*—Short and lobed (as illustrated).

*Texture.*—Fleshy.

*Serration.*—Medium.

*Shape of base.*—Rounded and tending to be slightly asymmetric.

*Apex.*—Cuspidate.

*Internode length.*—Very short to short, approximatley 1.5 cm. on average.

*Stems.*—Thin, average strength, round in cross section, nearest to Yellow-Green Group 144A in coloration, and commonly with slight anthocyanin coloration.

I claim:

1. A new and distinct cultivar of Chrysanthemum plant named 'Chakuse', substantially as herein shown and described, which (a) exhibits in profusion attractive double bright yellow spider blossoms with upright petals, (b) exhibits a flower response period of approximately eight and one-half weeks, (c) is highly amenable to branching by pinching, (d) achieves a short plant height, and (e) is particularly suited for pot mum production on a recurrent basis throughtout the year.

* * * * *